United States Patent

Nordan et al.

[11] Patent Number: 5,090,073
[45] Date of Patent: Feb. 25, 1992

[54] SURGICAL HEADREST

[76] Inventors: Lee T. Nordan, 5144 Triple Crown Row, Rancho Santa Fe, Calif. 92067; Roger J. Malcolm, 920-C Calle Negocio, San Clemente, Calif. 92672

[21] Appl. No.: 748,537

[22] Filed: Aug. 22, 1991

[51] Int. Cl.⁵ .................... A61G 7/06; A61G 13/00
[52] U.S. Cl. ........................ 5/640; 128/845; 128/202.18; 128/849; 269/328; 5/643; 5/639; 5/644
[58] Field of Search ........... 5/434, 436, 437, 440–442; 269/328; 128/847, 849, 857, 845, 202.18

[56] References Cited

U.S. PATENT DOCUMENTS

| | | | |
|---|---|---|---|
| 2,148,347 | 2/1939 | Gray | 128/845 X |
| 2,386,134 | 10/1945 | Mermis | 128/845 |
| 2,492,383 | 12/1949 | Jones | 5/437 X |
| 3,347,544 | 10/1967 | Uffendorfe | 128/847 X |
| 3,482,571 | 12/1969 | Behrendt | 5/436 X |
| 4,223,669 | 9/1980 | Morledge | 128/849 X |
| 4,545,572 | 10/1985 | Day | 269/328 |
| 4,979,519 | 12/1990 | Chavarria et al. | 269/328 X |
| 4,991,222 | 2/1991 | Nixdorf | 5/437 X |

Primary Examiner—Michael F. Trettel
Attorney, Agent, or Firm—Henri J. A. Charmasson

[57] ABSTRACT

An apparatus for immobilizing the head of a patient during ocular, facial, or dental surgery comprises a flat cushion headrest bordered by a neck-supporting bulge. Adjustable lateral head-clamping arms incorporate padded headphones. A shroud-supporting frame extends obliquely from each side of the headrest over the patient's chest area, and provides a means for mounting ventilation lines and sensors for patient monitoring.

10 Claims, 1 Drawing Sheet

5,090,073

SURGICAL HEADREST

FIELD OF THE INVENTION

This invention relates to operating tables and couches and associated accessories used to support and immobilize parts of the patient's anatomy during surgery.

BACKGROUND OF THE INVENTION

Ocular, facial, or dental care, including surgery is often performed under local anesthesia or mild sedation with the patient remaining alert throughout the therapeutic surgical operation. During delicate operations such as eye surgery, the patient's head must be totally immobilized. Lacking proper and efficient restraining devices, the physician must often resort to a general anesthesia or heavy sedation to guarantee the patient's immobility. The risks associated with general anesthesia and heavy sedation could be avoided with an effective head-restraining apparatus compatible with operating tables, or couches.

SUMMARY OF THE INVENTION

The main and secondary objects of the invention are to provide a comfortable, non-invasive, non-pin fixation head-restraining apparatus to be used in combination with an operating table which can assure complete immobility of the patient during delicate ocular operations and the like; and to provide a means of communication with the patient as well as offering sound entertainment to occupy the patient's mind during procedures.

These and other objects are achieved by means of an apparatus which may be laid upon a surgical table, and which comprises a cushion headrest bordered by a neck-supporting raised section shaped and dimensioned to slightly tilt the head of the patient backward. A clamping mechanism comprises two headphone-mounting arms which can be adjustably pressed against the patient's ears and temples.

DESCRIPTION OF THE PREFERRED EMBODIMENT OF THE INVENTION

Figure 1:
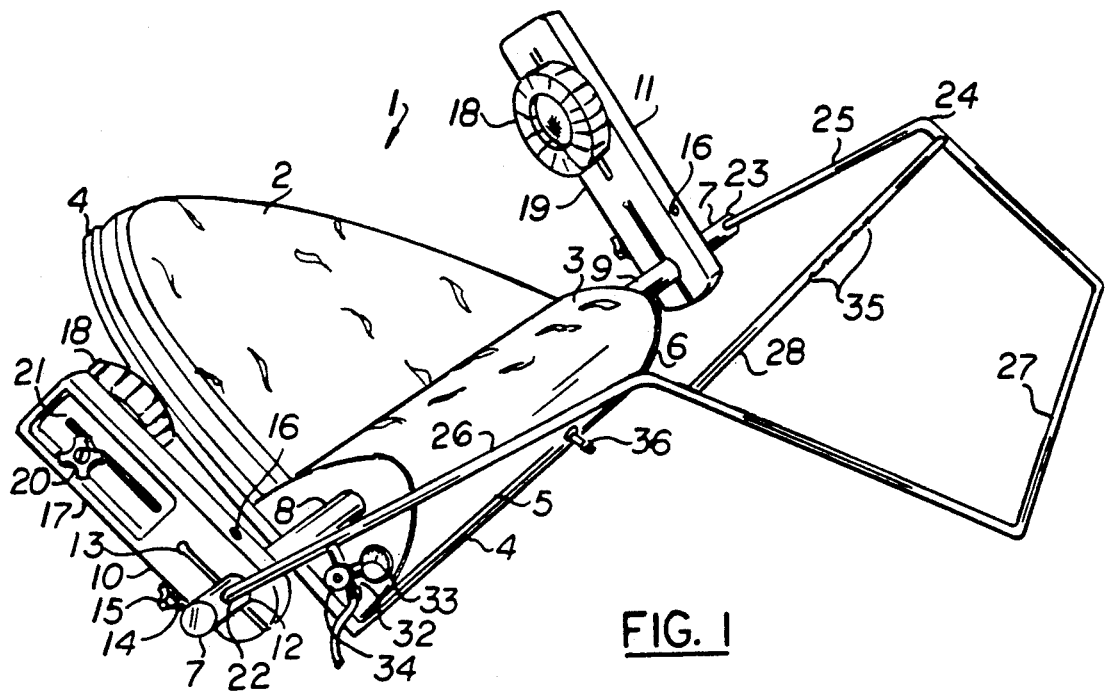
FIG. 1 is a perspective view of the preferred embodiment of the invention.

Referring now to the drawing, there is shown in FIG. 1 a head-restraining apparatus 1 specifically designed to lie on a surgical table. The apparatus comprises a substantially flat, cushioned or inflated headrest area 2 of a generally triangular shape which is bordered along its base by a neck-supporting, similarly cushioned bulge 3 shaped and dimensioned to fit against the nucha of the patient. The bulge may include a pneumatic bladder which can be adjustably inflated through valve 36 for optimum patient comfort. The height of the bulge 3 over the upper surface of the headrest 2 may lie between 5 and 8 centimeters, just enough to tilt the patient's head slightly backward when the base 4 of the apparatus rests on the flat top of the operating table. Two lateral walls 5 and 6 extend upwardly from the base 4 to frame the bulge 3, and support a horizontal shaft 7 with opposite ends 8 and 9 extending on either side of the bulge 3.

Two adjustable arms 10 and 11 are slidingly engaged on the respective ends of the shaft through a circular opening 12 intercepted by a slot running through the middle of one end of each arm 10, 11. Each arm can be clamped on the shaft in any radial or axial position by tightening a bolt equipped with a large head-knob 15, and engaged into a threaded bore 16 through the slotted part of the arm. The distal part 17 of each arm mounts an earmuff 18 adjustably placed against the side 19 of the arm facing the headrest 2. The distance between the center of the earmuff 18 and the shaft 7 can be adjusted by loosening the securing bolt 20 associated with the earmuff 18, and engaged into a longitudinal slot 21 spanning the distal half of the arm. Each earmuff 18 incorporates a earphone which may be connected to a sound system by means of a conductor not shown in the drawing or by means of a wireless link. Two bores 22, 23 drill transversally through opposite ends of the shaft 7, receive the end of a shroud-supporting frame 24. The frame comprises two arms 25, 26 extending obliquely from the shaft 7 over the patient's chest. The arms 25, 26 are joined in two places by two cross-members 27, 28 to form a support for a surgical shroud, and to provide oxygen ventilation as explained below.

Figure 2:
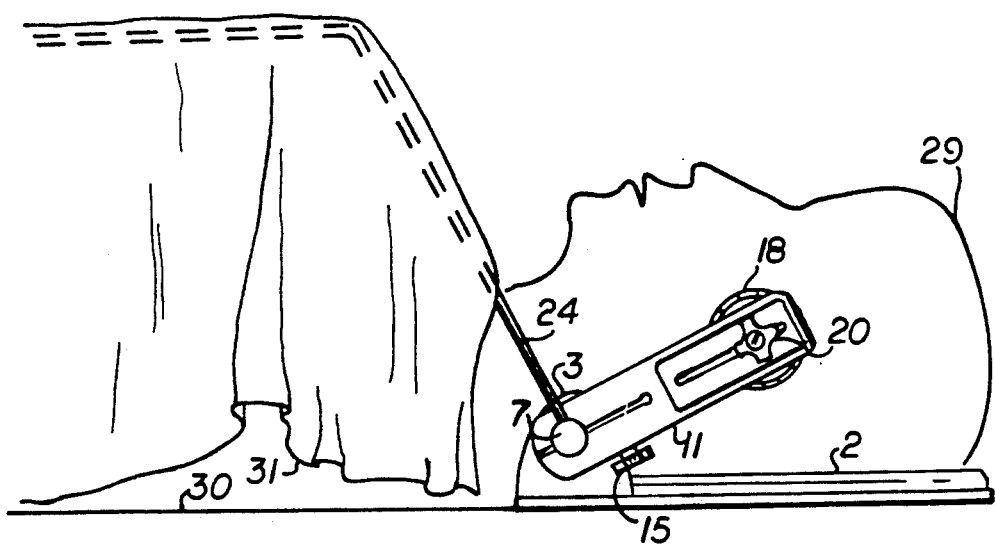
FIG. 2 is a lateral view thereof in use on a patient.

As shown in FIG. 2, once the patient's head 29 lies on the operating table 30 and headrest 2 the arms 10, 11 can be conveniently adjusted to bring the earmuffs 18 in intimate contact with the ears and temples of the patient. The clamping action of the arms prevent any lateral movement of the head. The height and position of the bulge 3 forces the head 29 into a slightly backward-tilted position which guarantees a maximum opening of the respirator tract, thus assuring comfort and proper ventilation. The speakers provide a means of communication whereby the surgeon may talk to the patient during procedures, while the piping of music or other sound entertainment during surgery occupies the mind of the patient, reducing nervous tension and minimizing the risk of facial movements. The fame 24 supports a shroud 31 over the patient's chest, but could also be turned around to support shrouds framing the patient's head.

The frame 24 may be used to anchor a ventilation line to free-blow oxygen air under said shroud. Alternatively, and as illustrated in FIG. 1, the frame can be made of tubular elements used to carry and dispense the oxygen under the shroud. An inlet port 32 with monitoring gauge 33 and control valve 34 are located on the base of one of the tubular arms 26. One of the tubular cross pieces 28 having bores 35 act as an oxygen distributing manifold. Additionally, oxygen and/or $CO_2$ sensors may be affixed to the frame for interfacing with patient monitoring and ventilation equipment.

While the preferred embodiment of the invention has been described, modifications can be made and other embodiments may be devised without departing from the spirit of the invention and the scope of the appended claims.

What is claimed is:

1. An apparatus for immobilizing the head of a patient during eye surgery and the like, which comprises:
    cushioned headrest defining a cervical bulge shaped and dimensioned to nest under the nucha of the patient;
    a shaft extending horizontally and laterally from opposite sides of said headrest;
    first and second arms pivotally and slidingly mounted on said shaft on opposite sides of said headrest;

each of said arms having a pad mounted on a side facing said headrest; and adjustable means for radially and axially positioning and immobilizing each arm on said shaft.

2. The apparatus of claim 1, wherein said headrest comprises a substantially flat cushion area contiguous to a raised edge, said raised edge forming said bulge.

3. The apparatus of claim 2, wherein each of said pads comprises a cushioned earmuff.

4. The apparatus of claim 3, which further comprises a shroud-holding frame extending from the sides of said headrest.

5. The apparatus of claim 4, wherein said frame comprises a pair of rods extending obliquely from opposite ends of said shaft over the patient's chest area.

6. The apparatus of claim 4, wherein said frame includes a means for supporting ventilation lines and monitor sensors.

7. The apparatus of claim 4, wherein said frame comprises a hollow tube having an inlet port for ventilation of gases and exhaust ports for delivery of said gases to the patient.

8. The apparatus of claim 3, wherein each of said earmuffs comprise an earphone.

9. The apparatus of claim 3, which further comprises means for adjusting the distance between said shaft and each of said earmuffs.

10. The apparatus of claim 9, wherein said headrest comprises a pneumatic bladder.

* * * * *